United States Patent [19]
Van Tuyl Cotter

[11] Patent Number: 6,090,806
[45] Date of Patent: Jul. 18, 2000

[54] FUNGICIDAL MIXTURES

[75] Inventor: Henry Van Tuyl Cotter, Ingelheim, Germany

[73] Assignee: American Cyanamid Company, Madison, N.J.

[21] Appl. No.: 09/143,806

[22] Filed: Aug. 31, 1998

[51] Int. Cl.⁷ .......................... A01N 43/76; A01N 31/535
[52] U.S. Cl. ........................................ 514/237.5; 514/376
[58] Field of Search ................................ 514/237.5, 376

[56] References Cited

U.S. PATENT DOCUMENTS

| | | | |
|---|---|---|---|
| 4,753,934 | 6/1988 | Nickl et al. ........................... | 514/231.5 |
| 5,262,414 | 11/1993 | Albert et al. ......................... | 514/237.5 |

FOREIGN PATENT DOCUMENTS 0 393 911 B1  8/1994  European Pat. Off. .

*Primary Examiner*—Allen J. Robinson
*Attorney, Agent, or Firm*—Barbara L. Renda

[57] ABSTRACT

The invention relates to fungicidal compositions comprising synergistically effective amounts of at least one acrylic acid morpholide of formula I

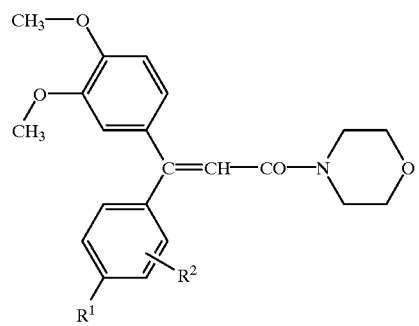

(I)

in which $R^1$ and $R^2$ have the meaning given in claim 1 and at least one fungicidal oxazolidinone of formula II

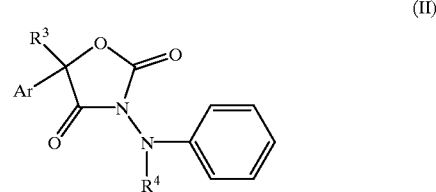

(II)

in which $R^3$, $R^4$ and Ar have the meaning given in claim 1, and to a method of controlling the growth of phytopathogenic fungi and/or the plant disease caused by them at a locus which comprises applying synergistically effective amounts of at least one acrylic acid morpholide of formula I (a) and at least one fungicidal compound of formula II (b) to the locus, together with a fungicidally acceptable carrier and/or surface active agent.

12 Claims, No Drawings

FUNGICIDAL MIXTURES

BACKGROUND OF THE INVENTION

The present invention relates to a fungicidal composition comprising synergistically effective amounts of
(a) at least one acrylic acid morpholide of formula I

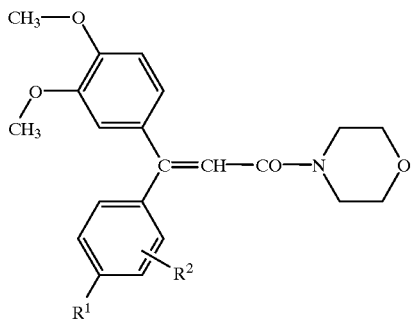

(I)

in which
R$^1$ and R$^2$ each independently represent hydrogen or halogen atom or an optionally substituted alkyl, alkenyl, alkynyl, alkadienyl, aryl, aryloxy, heteroaryl, cycloalkyl, cycloalkenyl, bicycloalkyl or heterocyclyl group,
(b) and at least one fungicidal oxazolidinone of formula II

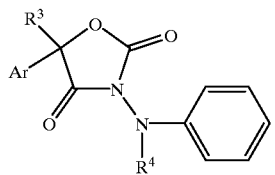

(II)

in which
R$^3$ and R$^4$ each independently represent hydrogen or an optionally substituted alkyl, alkenyl, alkynyl, alkadienyl, aryl, aryloxy, cycloalkyl, or cycloalkenyl group; and
Ar represents an optionally substituted phenyl group; together with a fungicidally acceptable carrier and/or surface active agent.

The fungicidal compounds of formula I useful in the present invention are known from European Patent No. 0 120 321. U.S. Pat. No. 5,262,414 discloses mixtures of these compounds with contact fungicides. EP 0 393 911 discloses the method of using oxazolidinones of formula II as fungicides, and indicates that they can be mixed with other fungicides, vacterisides, acaricides, etc., including 4-[3-(4-chlorophenyl)-3-(3,4-dimethoxyphenyl)-1-oxo-2-propenyl] morpholine, a compound of formula I. However, there is no suggestion that the compounds of formula I with oxazolidinones of formula II, when admixed in a tank mix or when co-formulated, would exhibit synergistic effects. Moreover, there is no suggestion that a composition comprising a synergistic mixture of these compounds can be advantageously be used for controlling plant diseases caused by ascomycetes, basidiomycetes, deuteromycetes and oomycetes, e.g. *Uncinula necator* and *Phytophthora infestans*.

A mixture of fungicides shows synergistic effect if the fungicidal activity of the mixture is larger than the sum of activities of the separately applied compounds. The expected fungicidal activity for a given mixture of two fungicides can be calculated as follows (See Colby, S. R., "Calculating synergistic and antagonistic response of herbicide combinations", Weeds 15, pp 20–22 (1967):

$$EE = x + y - x \cdot y/100$$

wherein
x is the efficacy in % compared with an untreated control upon treatment with a fungicidal active ingredient A at a dose rate a;
y is the efficacy in % compared with an untreated control upon treatment with a fungicidal active ingredient B at a dose rate b;
EE is the expected efficacy with a combination of fungicidal active ingredients A and B at a dose of a+b, respectively.
If the actual efficacy (E) exceeds the expected (calculated) one (EE), the mixture displays a synergistic effect.

SUMMARY OF THE INVENTION

The present invention relates to a fungicidal composition comprising synergistically effective amounts of at least one compound of formula I, and at least one compound of formula II, together with a fungicidally acceptable carrier and/or surface active agent.

The present invention also includes a method for controlling the growth of phythopathogenic fungi and/or of the plant disease caused by such fungi comprising application of synergistically effective amounts of at least one compound of formula I and at least one compound of formula II as defined above.

DETAILED DESCRIPTION OF THE PREFERRED EMBODIMENTS

Surprisingly, a clear synergy between the compounds of formula I and the compounds of formula II in greenhouse trials was found when these two compounds were tank mixed and when the activity of the combination was compared with that of each solo compound.

In general terms, unless otherwise stated, as used herein the term "halogen atom" denotes a bromine, iodine, chlorine or fluorine atom, and is especially a bromine, chlorine or fluorine atom, in particular, a bromine or chlorine atom.

"Optionally substituted" moieties may be unsubstituted or have from one up to the maximal possible number of substituents. Typically, 0 to 2 substituents are present. Each optionally substituted group can be independently substituted by one or more halogen atoms or nitro, cyano, cycloalkyl, preferably C$_{3-6}$ cycloalkyl, cycloalkenyl, preferably C$_{3-6}$ cycloalkenyl, haloalkyl, preferably C$_{1-6}$ haloalkyl, halocycloalkyl, preferably C$_{3-6}$ halocycloalkyl, alkoxy, preferably C$_{1-6}$ alkoxy, haloalkoxy, preferably C$_{1-6}$ haloalkoxy, phenyl, halo- or dihalo-phenyl or pyridyl groups.

In general terms, unless otherwise stated herein, the terms "alkyl", "alkenyl", "alkynyl", "alkadienyl" and "alkoxy" as used herein with respect to a radical or moiety refer to a straight or branched chain radical or moiety. As a rule, such radicals have up to 10, in particular up to 6 carbon atoms. Preferably, an alkyl or alkoxy moiety has from 1 to 6, carbon atoms, preferably, from 1 to 5 carbon atoms. A preferred alkyl moiety is the methyl, ethyl, n-propyl, isopropyl or n-butyl group.

In general terms, unless otherwise stated herein, the term "aryl", as used herein with respect to a radical or moiety refers to an aryl group having 6, 10 or 14 carbon atoms, preferably 6 or 10 carbon atoms, in particular, phenyl being optionally substituted by one or more halogen atoms, nitro, cyano, alkyl, preferably $C_{1-6}$ alkyl, alkoxy, preferably $C_{1-6}$ alkoxy, haloalkyl, preferably $C_{1-6}$ haloalkyl, haloalkoxy, preferably $C_{1-6}$ haloalkoxy groups.

In general terms, unless otherwise stated herein, the term "cycloalkyl" or "cycloalkenyl", as used herein with respect to a radical or moiety refers to a cycloalkyl group having 3 to 8 carbon atoms or a cycloalkenyl group having 5 to 8 carbon atoms, preferably 5 to 7 carbon atoms, in particular, cyclopentyl, cyclohexyl or cyclohexenyl being optionally substituted by one or more halogen atoms, nitro, cyano, alkyl, preferably $C_{1-6}$ alkyl, alkoxy, preferably $C_{1-6}$ alkoxy.

The following compounds of formula I are preferred:

| $R^1$ | $R^2$ |
|---|---|
| Cl | H |
| Br | H |
| $CF_3$ | H |
| $CF_3O$ | H |
| propyl | H |
| butoxy | H |
| phenyl | H |
| 4-chlorophenoxy | H |
| H | 3-phenoxy |

Particularly preferred compounds of formula I are those wherein $R^1$ represents a halogen atom and $R^2$ represents a hydrogen atom.

A particularly preferred compound of formula I is dimethomorph, which is known from the "The Pesticide Manual", 10th Edition, The British Crop Protection Council and The Royal Society of Chemistry, 1994, (hereinbelow referred to as "Pesticide Manual"), page 236.

Preferred are the those compounds of formula II, wherein $R^3$ represents a hydrogen atom or a $C_{1-4}$ alkyl group, in particular a methyl group, $R^4$ represents a hydrogen atom, and Ar represents a phenyl group, optionally or substituted in the 4-position by a halogen atom or an alkyl, alkoxy, alkenyloxy, phenyl or phenoxy group.

The following compounds of formula II are preferred:

| $R^3$ | $R^4$ | Ar |
|---|---|---|
| $CH_3$ | H | 4-phenoxyphenyl |
| $CH_3$ | H | phenyl |
| $CH_3$ | H | 4-oct-2-enyloxyphenyl |
| H | H | 4-phenoxyphenyl | particularly preferred compound of formula II is famoxadone, which is known from the "The Pesticide Manual", page 500.

Preferred are co-formulations, comprising:

an acrylic acid morpholide of formula I, in particular, dimethomorph;

at least one oxazolidone of formula II;in particular, famoxadone, a surface active agent;

optionally a foam breaking agent, in particular, a mixture of perfluoroalkyphosphonic acids and/or perfluoroalkylphosphinic acids, in particular Defoamer® SF or Fluowett® PL, which are commercially available from Clariant GmbH (former Hoechst AG), Germany.

The compounds of formulae I and II are to be applied together, in synergistically effective amounts. They exhibit an extraordinary efficacy against a broad range of phytopathogenic fungi. They may be applied as foliar or soil fungicide.

The mixture according to the invention may be preferably applied for controlling diseases caused by phytopathogenic fungi of the genera of Phythophthora, Plasmopara, Pseudoperonospora, Bremia, Peronospora, Alterna, Guignardia, Septoria, Botrytis, Phomopsis, Puccinia, Rhizoctonia, and in particular, of the species *Phythophthora infestans* and other oomycetes.

The application rate of the compound of formula I according to this invention is usually in the range of 5 to 2000 grams of active ingredient (g a.i.) per hectare, with rates between 50–500 g a.i./ha often achieving satisfactory control. The optimal rate for a specific application will depend on the crop(s) under cultivation and the predominant species of infesting fungus, and readily may be determined by established biological tests known to those skilled in the art.

In general, the preferred application rate of the compound of formula II is in the range of 20 to 500 g a.i./ha, preferably 50–200 g a.i./ha.

The optimal rate for the second fungicidal compound, in particular famoxadone will, however, depend on the crop(s) under cultivation and the level of infestation by the fungus, and can readily be determined by established biological tests.

The ratio (by weight) of the compound of formula I to the compound of formula II, in particular, famoxadone, is as a rule, from about 1:100 to 100:1. The preferred ratio formula I:formula II compound may vary, e.g., from about 1:10 to about 10:1, in particular, from about 1:2 to about 2:1, and most preferably is about 1:1.

The active compounds will be formulated together in a suitable ratio according to the present invention, together with usual carriers and/or additives known in the art.

Accordingly the invention further provides a concentrated fungicidal composition which comprises a carrier and, as active ingredient, at least one compound of formula I and at least one compound of formula II as defined above, in particular, dimethomorph and famoxadone.

A method of making such a composition is also provided which comprises bringing the compounds of formulae I and II as defined above into association with at least one carrier. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may, for example, be a plant, seed or soil, or to facilitate storage, transport or handling. A carrier may be a solid or a liquid, including material which is normally a gas but which has been compressed to form a liquid.

The compositions may be manufactured into, for instance, emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as solvents, solid carriers, surface active compounds (surfactants), and optionally, solid and/or liquid auxiliaries and/or adjuvants. The form of application such as spraying, atomizing, dispersing or pouring may be chosen according to the desired objectives and the given circumstances.

Typical solvents are aromatic hydrocarbons, e.g., Solvesso®, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g., n-octylpyrrolidone or cyclohexylpyrrolidone, epoxidized plant oil esters, e.g. methylated coconut or soybean oil ester and water. Mixtures of different liquids are often suitable.

Solid carriers, which are used to prepare dusts, wettable powders, water dispersible granules, or granules, can be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also include mixtures of individual surfactants.

The compositions of the invention may, for example, be formulated as solutions, emulsifiable concentrates, emulsions, suspension concentrates and aerosols. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents, such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example, compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected as disclosed, for example, by U.S. Pat. No. 5,705,174.

The biological activity of the active ingredients can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredients. Preferably, linoleic acid is used as adjuvant.

Examples of formulations according to the invention are:

| Emulsion Concentrate (EC) | | |
|---|---|---|
| active ingredient | dimethomorph/famoxadone (1:1 w/w) | 30% (w/v) |
| emulsifier(s) | Atlox ® 4856 B and Atlox ® 4857 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| solvent | Shellsol ® A[2] (mixture of $C_9$–$C_{10}$ aromatic hydrocarbons) | to 1000 ml |
| Suspension Concentrate (SC) | | |
| active ingredient | dimethomorph/famoxadone (1:1 w/w) | 50% (w/v) |
| dispersing agent | Soprophor ® FL 3) (polyoxyethylene polyaryl phenyl ether phosphate amine salt) | 3% (w/v) |
| antifoaming agent | Rhodorsil ® 422[3] (nonionic aqueous emulsion of polydimethylsiloxanes) | 0.2% (w/v) |
| structure agent | Kelzan ® S[4] (Xanthan gum) | 0.2% (w/v) |
| antifreezing agent | Propylene glycol | 5% (w/v) |
| biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | dimethomorph/famoxadone (1:1 w/w) | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates) | 3% (w/w) |
| Carrier/Filler | Kaolin | 35% (w/w) |
| Water Dispersible Granules (WG) | | |
| Active Ingredient | dimethomorph/famoxadone (1:1 w/w) | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |

| | -continued | |
|---|---|---|
| Antifoaming agent | Rhodorsil ® EP 6703[3]<br>(encapsulated silicone) | 1% (w/w) |
| Disintegrant | Agrimer ® ATF[7]<br>(cross-linked homopolymer<br>of N-vinyl-2-<br>pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products A concentrated composition according to the invention preferably contains from 0.5% to 95% by weight of active ingredients.

As a commodity, the compositions are preferably in a concentrated form, whereas an end-user will generally employ diluted compositions. The compositions may be diluted to a concentration of 0.001% of active ingredients. The doses usually are in the range from 0.01 to 10 kg a.i./ha.

The compositions of this invention can be applied to the plants or their environment simultaneously with, or in succession to, other active substances. These other active substances can be either fertilizers, agents which donate trace elements or other preparations which influence plant growth. However, they can also be selective herbicides, insecticides, fungicides, bactericides, nematicides, algicides, inolluseidides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

In an alternative preferred embodiment the active ingredients are added to the tank mix together each as a solo formulation.

Therefore, a further embodiment of the present invention is a kit for the preparation of a spray mixture consisting of two separate containers:
(i) a container which comprises at least one fungicide of formula I, in particular dimethomorph, conventional adjuvants and carriers;
(ii) a container which comprises at least one compound of formula II, in particular famoxadone, conventional adjuvants and carriers.

In a preferred embodiment the said kit will consist of two bottles with dispensing means which allow the easy and correct addition of the active ingredients (a) and (b) to the tank mix.

For a clearer understanding of the invention, a specific example is set forth below. This example is merely an illustration and is not to be understood as limiting the scope and underlying principles of the invention in any way. Various modifications of the invention in addition to those shown and described herein will become apparent to those skilled in the art from the following example and foregoing description. Such modifications are also intended to fall within the scope of the appended claims.

The test results described below demonstrate the enhancement of efficacy (synergy) obtained when compounds of formula I(a) are used in combination with compounds of formula II(b).

EXAMPLE 1

For the greenhouse study, technical dimethomorph and famoxadone were used.

Potato plants var. 'Bintje' were grown in small pots to the 6–8 leaf stage from sprout cuttings. Technical materials were formulated in 5% acetone 0.05% TWEEN 20 water and applied with a fungicide sprayer with three lateral nozzles to near runoff; the plants rotated on a turntable in the spray cabin during application. Each compound was applied singly at multiple rates and the two compounds were applied together in equal amounts (1:1 ratio) at multiple rates. After application, the plants were allowed to air dry and returned to the greenhouse. One day after application the plants were inoculated with a sporangial zoospore suspension of *Phytophthora infestans*. The plants were then kept in a moist infection chamber in which the relative humidity was maintained at 100% for 2 days. Then the plants were returned to a greenhouse until symptoms developed.

Disease symptoms (potato late blight) were assessed 7 days after application of the compounds. The disease control efficacy of the products was calculated in relation to the disease level on the untreated plants. The results of this evaluation are shown in the following table.

TABLE

Disease control

| | | Potato late blight<br>1 day residual test<br>efficacy (%) | |
|---|---|---|---|
| Treatment | dose (ppm) | actual<br>efficacy | expected<br>efficacy* |
| dimethomorph | 9 | 91 | — |
| | 3 | 76 | |
| | 1 | 68 | |
| | 0.3 | 47 | |
| famoxadone | 9 | 69 | — |
| | 3 | 39 | |
| | 1 | 19 | |
| | 0.3 | 16 | |
| dimethomorph + | 9 + 9 | 95 | 97 |
| famoxadone | 3 + 3 | 90 | 85 |
| | 1 + 1 | 86 | 74 |
| | 0.3 + 0.3 | 68 | 55 |

*Expected efficacy calculated using the Colby Formula as given hereinbefore.

Whereas the expected disease control efficacies for the mixture of dimethomorph and famoxadone were 55%, 74% and 85% for mixtures of 0.3+0.3 ppm, 1+1 ppm, and 3+3 ppm, the respective actual disease control efficacies were all higher: 68%, 86% and 90% respectively. Thus the efficacy of the combination was higher than could have been expected from the additive efficacy of the two compounds providing clear evidence that synergism occurred between dimethomorph and famoxadone.

What is claimed is:
1. A fungicidal composition for the control of the growth of *Phytophthora infestans* comprising synergistically effective amounts of

(a) at least one acrylic acid morpholide of formula I

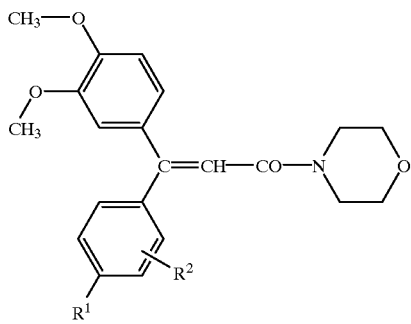

(I)

in which

R¹ represents a hydrogen or halogen atom or an optionally substituted alkyl, alkoxy, alkenyl, alkynyl, alkadienyl, aryl, aryloxy, cycloalkyl, cycloalkenyl, group, and R² represents a hydrogen atom, or R¹ represents a hydrogen atom and R² represents a 3-phenoxy group.

(b) and at least one fungicidal oxazolidinone of formula II

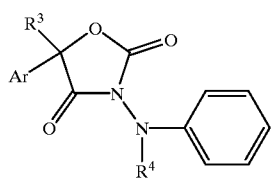

(II)

in which

R³ and R⁴ each independently represent hydrogen or an optionally substituted alkyl, group; and Ar represents an optionally substituted phenyl group, together with a fungicidally acceptable carrier and/or surface active agent.

2. A compositions according to claim 1 wherein the compound of formula I is dimethomorph.

3. A composition according to claim 1, wherein the compound of formula II is famoxadone.

4. A composition according to claim 1, wherein the ratio (by weight) of the acrylic acid amide of formula I to the compound of formula II is from about 0.01:1 to 100:1.

5. A composition according to claim 1 wherein the compound of formula I is dimethomorph, the compound of formula II is famoxadone and the ratio (by weight) of dimethomorph is about 1:1.

6. A composition according to claim 1 wherein the compounds of formula I is dimethomorph and the compound of formula II is famoxadone.

7. A method of controlling the growth of *Phytophthora infestans* phythopathogenic fungi at a locus which comprises applying an amount sufficient to control said fungi of a composition as claimed in claim 1 to the locus.

8. A method according to claim 7 wherein the compound of formula I is dimethomorph.

9. A method according to claim 7 wherein the compound of formula II is famoxadone.

10. A method according to claim 7 wherein the ratio (by weight) of the acrylic acid amide of formula I to the compound of formula II compound is from about 0.01:1 to 100:1.

11. A method according to claim 7 wherein the compound of formula I is dimethomorph and the compound of formula II is famoxadone and the ratio of dimethomorph to famoxadone is about 1:1.

12. A method according to claim 7 wherein the compounds of formula I is dimethomorph and the compound of formula II is famoxadone.

* * * * *